(12) United States Patent
Harley et al.

(10) Patent No.: US 7,736,641 B2
(45) Date of Patent: Jun. 15, 2010

(54) ROLE FOR SRY IN PARKINSON'S DISEASE

(75) Inventors: Vincent Russel Harley, Victoria (AU); Eric J. N. Vilain, Los Angeles, CA (US)

(73) Assignee: Prince Henry's Institute of Medical Research, Clayton, Victoria (AU)

(*) Notice: Subject to any disclaimer, the term of this patent is extended or adjusted under 35 U.S.C. 154(b) by 401 days.

(21) Appl. No.: 11/677,474

(22) Filed: Feb. 21, 2007

(65) Prior Publication Data

US 2008/0199432 A1    Aug. 21, 2008

(51) Int. Cl.
*A01N 65/00* (2006.01)
(52) U.S. Cl. .................. 424/93.2; 424/93.21; 435/320.1
(58) Field of Classification Search ........................ None
See application file for complete search history.

(56) References Cited

U.S. PATENT DOCUMENTS 5,175,103 A * 12/1992 Lee et al. ..................... 435/455
7,011,827 B2    3/2006 Lee et al.

OTHER PUBLICATIONS

Su et al. Am J Hum Genet 1993;52:24-38.*
Hacker et al., "Expression of Sry, the mouse sex determining gene" Development, 121:1603-1614 (1995).
Hargrave et al., "Expression of the Sox11 Gene in Mouse Embryos Suggests Roles in Neuronal Maturation and Epithelio- Mesenchymal Induction" Developmental Dynamics, 210:79-86 (1997).
Harley et al., "DNA Binding Activity Recombinant SRY from Normal Males and XY Females" Science, 255 (5043):453-456 (1992).
Iacovitti et al., "Expression of tyrosine hydroxylase in newly differentiated neurons from a human cell line (hNT)" NeuroReport, 8:1471-1474 (1997).
Ivanova et al., "Estrogen Regulates Tyrosine Hydroxylase Expression in the Neonate Mouse Midbrain" J. Neurobiol., 54:638-647 (2003).
Jeske et al., "Expression of a linear Sry transcript in the mouse genital ridge" Nature Genetics, 10:480-482 (1995).
King et al., "The SRY high-mobility-group box recognizes DNA by partial intercalation in the minor groove: A topological mechanism of sequence specificity" Proc. Natl. Acad. Sci. USA, 90:11990-11994 (1993).
Koopman et al., "Expression of a candidate sex-determining gene during mouse testis differentiation" Nature, 348:450-452 (1990).
Koopman et al., "Male development of chromosomally female mice transgenic for Sry" Nature, 351:117-121 (1991).
Kumer et al., "Intricate Regulation of Tyrosine Hydroxylase Activity and Gene Expression" Journal of Neurochemistry, 67(2):443-462 (1996).
Lahr et al., "Transcription of the Y chromosomal gene, Sry, in adult mouse brain" Molecular Brain Research, 33:179-182 (1995).
Landgraf, R., "Antisense targeting in behavioral neuroendocrinology" Journal of Endocrinology, 151:333-340 (1996).
Laudet et al., "Ancestry and diversity of the HMG box superfamily" Nucleic Acids Research, 21(10):2493-2501 (1993).
Lee et al., "Differentiation of NTERA-2 Clonal Human Embryonal Carcinoma Cells into Neurons Involves the Induction of All Three Neurofilament Proteins" The Journal of Neuroscience, 6(2):514-521 (1996).
Leranth et al., "Estrogen Is Essential for Maintaining Nigrostriatal Dopamine Neurons in Primates: Implications for Parkinson's Disease and Memory" The Journal of Neuroscience, 20(23):8604-8609 (2000).
Lindvall et al., "Transplantation in Parkinson's Disease: Two Cases of Adrenal Medullary Grafts to the Putamen" Ann. Neurol., 22:457-468 (1987).
Madrazo et al., "Open Microsurgical Autograft of Adrenal Medulla to the Right Caudate Nucleus in Two Patient With Intractable Parkinson's Disease" The New England Journal of Medicine, 316(14):831-834 (1987).
Maharjan et al., "Transcriptional regulation of tyrosine hydroxylase by estrogen: opposite effects with estrogen receptors a and b and interactions with cyclic AMP" Journal of Neurochemistry, 93:1502-1514 (2005).
Malbon, Craig C., "Frizzleds: New Members of the Superfamily of G-Protein-Coupled Receptors" Bioscience, 9:1048-1058 (2004).
Abraham et al., "Increased PKA and PKC Activities Accompany Neuronal Differentiation of NT2/D1 Cells" Journal of Neuroscience Research, 28:29-30 (1991).
Andrews et al., "Pluripotent Embryonal Carcinoma Clones Derived from the Human Teratocarcinoma Cell Line Tera-2" Laboratory Investigation, 50(2):147-162 (1984).
Andrews, Peter W., "Retinoic Acid Induces Neuronal Differentiation of a Cloned Human Embryonal Carcinoma Cell Line in Vitro" Developmental Biology, 103:285-298 (1984).
Andrews et al., "The expression of MHC antigens by human teratocarcinoma derived cell lines" Tissue Antigen, 17:493-500 (1981).
Bani-Yaghoub et al., "Human NT2/D1 cells differentiate into functional astrocytes" Development Neuroscience, 10 (18)3843-3846 (1999).
Becker, Jill B., "Gender Differences in Dopaminergic Function in Striatum and Nucleus Accumbens" Pharmacology Biochemistry and Behavior, 64(4):803-812 (1999).
Carruth et al., "Sex chromosome genes directly affect brain sexual differentiation" Nature Neuroscience, 5 (10):933-934 (2002).
Castelo-Branco et al., "GSK-3B inhibition/B-catenin stabilization in ventral midbrain precursors increases differentiation into dopamine neurons" Journal of Cell Science, 117:5731-5737 (2004).
Castillo et al., "Dopamine Biosynthesis Is Selectively Abolished in Substantia Nigra/Ventral Tegmental Area but Not in Hypothalmic Neurons in Mice with Targeted Disruption of the Nurr1 Gene" Molecular and Cellular Neuroscience, 11:36-46 (1998).

(Continued)

*Primary Examiner*—Q. Janice Li
(74) *Attorney, Agent, or Firm*—Karl Bozicevic; Bozicevic, Field & Francis LLP

(57) ABSTRACT

The present invention relates to a method for treating or preventing Parkinson's disease in a patient, the method comprising administering to the patient a therapeutically effective population of neuronal cells transformed with a nucleic acid molecule encoding SRY, wherein the transformed cells express SRY.

18 Claims, 9 Drawing Sheets

OTHER PUBLICATIONS

Castner et al., "Sex differences in striatal dopamine: in vivo microdialysis and behavioral studies" Brain Research, 610:127-134 (1993).

Cheung et al., "Identification of Candidate Genes Induced by Retinoic Acid in Embryonal Carcinoma Cells" Journal of Neurology, 68(5):1882-1888 (1997).

Dewing et al., "Direct Regulation of Adult Brain Function by the Male Specific Factor SRY" Current Biology, 16:415-420 (2006).

Dluzen et al., "Estrogen As a Modulator of Striatal Dopaminergic Neurotoxicity" Advantage in Neurodegenerative Disorders vol. 1: Parkinson's Disease, Edited by Joe Marwah and Herman Teitelbaum, Chapter 5, pp. 102-146, 1996.

Fernandez-Ruiz, et al., "Nigrostriatal and mesolimbic dopaminergic activities were modified throughout the ovarian cycle of female rats" J. Neural. Transm., 85:223-229 (1991).

Ferrari et al., "SRY, like HMG1, recognizes sharp angles in DNA" The EMBO Journal, 11(12):4497-4506 (1992).

Fleming et al., "Behavioral and immunohistochemical effects of chronic intravenous and subcutaneous infusions of varying doses of rotenone" Experimental Neurology, 187:418-429 (2004).

Gao et al., "Retinoic Acid Induction of Calcium Channel Expression in Human NT2N Neurons" Biochemical and Biophysical Research Communications, 247:407-413 (1998).

Gonzalez-Hernandez, et al., "Compartmental Organization and Chemical Profile of Dopaminergic and GABAergic Neurons in the Substantia Nigra of the Rat" The Journal of Comparative Neurology, 421:107-135 (2000).

Gundersen et al., "The new stereological tools: Disector, fractionator, nucleator and point sampled intercepts and their use in pathological research and diagnosis." APMIS, 96:857-881 (1998).

Mayer et al., "The Y-chromosomal genes SRY and ZFY are transcribed in adult human brain" Neurogenetics, 1:281-288 (1998).

Mayer et al., "Developmental profile of Sry transcripts in mouse brain" Neurogenetics, 3:25-30 (2000).

Misiuta et al., "The transcription factor Nurr1 in human NT2 cells and hNT neurons" Developmental Brain Research, 145:107-115 (2003).

Moon et al., "WNT and B-Catenin Signalling: Diseases and Therapies" Nature, 5:689-699 (2004).

Nasrin et al., "DNA-binding properties of the product of the testis-determining gene and a related protein" Nature, 354:317-320 (1991).

Nusse, Roel, "Wnts and Hedgehogs: lipid-modified proteins and similarities in signaling mechanisms at the cell surface" Development, 130:5297-5305 (2003).

Olanow et al., "Etiology and Pathogenesis of Parkinson's Disease" Ann. Rev. Neurosci., 22:123-44 (1999).

Pevny et al., "Sox genes find their feet" Current Opinion in Genetics & Development, 7:338-344 (1997).

Pleasure et al., "Pure, Postmitotic, Polarized Human Neurons Derived from NTera 2 Cells Provide a System for Expressing Exogenous Proteins in Terminally Differentiated Neurons" The Journal of Neuroscience, 12(5):1802-1815 (1992).

Pompolo et al., "Localisation of the SRY-related HMG box protein, SOX9, in rodent brain" Brain Research, 906:143-148 (2001).

Reisert et al., "Sexual differentiation of central catecholamine systems" Chp. 19, pp. 453-462, 1994.

Rex et al., "cSox21 exhibits a complex and dynamic pattern of transcription during embryonic development of the chick central nervous system" Mechanisms of Development, 66:39-53 (1997).

Saunders-Pullman, Rachel, "Estrogens and Parkinson Disease" Endocrine, 21(1):81-87 (2003).

Schallert, et al., "CNS plasticity and assessment of forelimb sensorimotor outcome in unilateral rat models of stroke, cortical ablation, parkinsonism and spinal cord injury" Neuropharmacology, 39:777-787 (2000).

Serova et al., "Response of tyrosine hydroxylase and GTP cyclohydrolase I gene expression of estrogen in brain catecholaminergic regions varies with mode of administration" Brain Research, 1015:1-8 (2004).

Sherwin, Ph.D., Barbara B., "Estrogen effects in cognition in menopausal women" American Academy of Neurology, 48(Suppl 7):S21-S26 (1997).

Singer et al., "Modulation of Bcl-2 expression: a potential component of estrogen protection in NT2 neurons" NeuroReport, 9:2565-2568 (1998).

Stambolic et al., "Lithium inhibits glycogen synthase kinase-3 activity and mimics Wingless signalling in intact cells" Current Biology, 6(12):1664-1668 (1996).

Trojanowski et al., "Transfectable and Transplantable Postmitotic Human Neurons: A Potential "Platform" for Gene Therapy of Nervous System Disorders" Experimental Neurology, 144:92-97 (1997).

Uwanogho et al., "Embryonic expression of the chicken Sox2, Sox3 and Sox11 genes suggests an interactive role in neuronal development" Mechanism of Development, 49:23-36 (1995).

Vadasz et al., "Genetic Effects and Sexual Dimorphism in Tyrosine Hydroxylase Activity in Two Mouse Strains and Their Reciprocal F1 Hybrids" Journal of Neurogenetics, 2:219-230 (1985).

Vadasz et al., "Perinatal Anti-androgen Treatment and Genotype Affect the Mesotelenephalic Dopamine System and Behavior in Mice" Hormones and Behavior, 22:528-539 (1988).

Wegner, Michael, "From head to toes: the multiple facets of Sox proteins" Nucleic Acids Research, 27 (6):1409-1420 (1999).

Whishaw et al., "Analysis of limb use by control rats and unilateral DA-depleted rats in the Montoya staircase test: movements, impairments and compensatory strategies" Behavioral Brain Research, 89:167-177 (1997).

Younkin et al., "Inducible expression of neuronal glutamate receptor channels in the NT2 human cell line" Proc. Natl. Acad. Sci. USA, 90:2174-2178 (1993).

Zigova et al., "Lithium Chloride Induces the Expression of Tyrosine Hydroxylase in hNT Neurons" Experimental Neurology, 157:251-258 (1999).

Zigova et al., "Apoptosis in cultured hNT neurons" Developmental Brain Research, 127:63-70 (2001).

Backlund et al., "Transplantation of adrenal medullary tissue to striatum in parkinsonism" J. Neurosurg., 62:169-173 (1985).

Dluzen et al., "Developmental and Genetic Influences upon Gender Differences in Methamphetamine-Induced Nigrostriatal Dopaminergic Neurotoxicity" Ann. N.Y. Acad. Sci., 1025:205-220 (2004).

Kleppner et al., "Long-Term Survival and Matruation of Neurons Derived from the Human Cell Line N-Tera 2 After Transplantation into Nude Mouse Brain" Transplantation, 732, Neuronsci. Abst., 1992, 18:782.

* cited by examiner

ROLE FOR SRY IN PARKINSON'S DISEASE

FIELD OF THE INVENTION

The present invention relates to neuronal cells transformed with a nucleic acid molecule encoding sex determining protein (SRY), which cells express SRY. The present invention also relates to a method for treating or preventing Parkinson's disease in a patient comprising administering to the patient neuronal cells which express SRY.

BACKGROUND OF THE INVENTION

The primary event of sexual development in mammals is the development of the gonadal sex from a bipotential and undifferentiated gonad into either testes or ovaries. This process, known as sex determination, is triggered by the SRY gene (Sex-determining Region, Y chromosome). Evidence that Sry was sex determining initially came from the microinjection of a 14.6 kb genomic DNA sequence containing the mouse Sry gene into chromosomally female embryos. The resulting transgenic mice developed phenotypically as males [Koopman, P., J. Gubbay, N. Vivian, P. Goodfellow, and R. Lovell-Badge, Male development of chromosomally female mice transgenic for Sry. Nature, 1991. 351(6322): p. 117-21]. Sry belongs to the Sox (Sry-box) family, whose members are characterised by a common HMG (high mobility group) DNA-binding motif [Laudet, V., D. Stehelin, and H. Clevers, Ancestry and diversity of the HMG box superfamily. Nucleic Acids Res, 1993. 21(10): p. 2493-501; Wegner, M., From head to toes: the multiple facets of Sox proteins. Nucleic Acids Res, 1999. 27(6): p. 1409-20]. Sox genes have been documented in a wide range of developmental processes, including neurogenesis (Sox2, 3 and 10) [Hargrave, M., E. Wright, J. Kun, J. Emery, L. Cooper, and P. Koopman, Expression of the Sox11 gene in mouse embryos suggests roles in neuronal maturation and epithelio-mesenchymal induction. Dev Dyn, 1997. 210(2): p. 79-86; Rex, M., D. A. Uwanogho, A. Orme, P. J. Scotting, and P. T. Sharpe, cSox21 exhibits a complex and dynamic pattern of transcription during embryonic development of the chick central nervous system. Mech Dev, 1997. 66(1-2): p. 39-53; Uwanogho, D., M. Rex, E. J. Cartwright, G. Pearl, C. Healy, P. J. Scotting, and P. T. Sharpe, Embryonic expression of the chicken Sox2, Sox3 and Sox11 genes suggests an interactive role in neuronal development. Mech Dev, 1995. 49(1-2): p. 23-36] and sex determination (Sox9). In addition, mutational analysis has suggested a role for Sox genes in influencing cell fate decisions during development [Pevny, L. H. and R. Lovell-Badge, Sox genes find their feet. Curr Opin Genet Dev, 1997. 7(3): p. 338-44]. Encoding a 204 amino acid protein, SRY is thought to bind and sharply bend DNA by means of its HMG box to regulate male-specific gene expression [Ferrari, S., V. R. Harley, A. Pontiggia, P. N. Goodfellow, R. Lovell-Badge, and M. E. Bianchi, SRY, like HMG1, recognizes sharp angles in DNA. Embo J, 1992. 11(12): p. 4497-506; Harley, V. R., D. I. Jackson, P. J. Hextall, J. R. Hawkins, G. D. Berkovitz, S. Sockanathan, R. Lovell-Badge, and P. N. Goodfellow, DNA binding activity of recombinant SRY from normal males and XY females. Science, 1992. 255(5043): p. 453-6; King, C. Y. and M. A. Weiss, The SRY high-mobility-group box recognizes DNA by partial intercalation in the minor groove: a topological mechanism of sequence specificity. Proc Natl Acad Sci USA, 1993. 90(24): p. 11990-4; Nasrin, N., C. Buggs, X. F. Kong, J. Camazza, M. Goebl, and M. Alexander-Bridges, DNA-binding properties of the product of the testis-determining gene and a related protein. Nature, 1991. 354 (6351): p. 317-20]. The transient expression of Sry during a brief period in the developing genital ridge, between embryonic days E10.5 and E12.5, is what triggers testis development from a bipotential gonad [Koopman, P., A. Munsterberg, B. Capel, N. Vivian, and R. Lovell-Badge, Expression of a candidate sex-determining gene during mouse testis differentiation. Nature, 1990. 348(6300): p. 450-2]. After this strictly regulated window of expression in mouse fetal gonads, Sry is re-expressed in the adult testis. However, while Sry RNA is expressed in the developing genital ridges as a linear transcript of about 5 kb [Hacker, A., B. Capel, P. Goodfellow, and R. Lovell-Badge, Expression of Sry, the mouse sex determining gene. Development, 1995. 121(6): p. 1603-14; Jeske, Y. W., J. Bowles, A. Greenfield, and P. Koopman, Expression of a linear Sry transcript in the mouse genital ridge. Nat Genet, 1995. 10(4): p. 480-2], in adult germ cells Sry RNA is expressed a circular transcript of about 1.3 kb, presumably untranslatable because not associated with ribosomes [Capel, B., A. Swain, S. Nicolis, A. Hacker, M. Walter, P. Koopman, P. Goodfellow, and R. Lovell-Badge, Circular transcripts of the testis-determining gene Sry in adult mouse testis. Cell, 1993. 73(5): p. 1019-30].

In addition to the gonads, Sry expression has been discovered in both the adult and embryonic mouse brain. For instance, the hypothalamus and the mesencephalon (midbrain) were both positive for Sry expression in RT-PCR experiments [Lahr, G., S. C. Maxsoni, A. Mayer, W. Just, C. Pilgrim, and I. Reisert, Transcription of the Y chromosomal gene, Sry, in adult mouse brain. Brain Res Mol Brain Res, 1995. 33(1): p. 179-82; Mayer, A., G. Lahr, D. F. Swaab, C. Pilgrim, and I. Reisert, The Y-chromosomal genes SRY and ZFY are transcribed in adult human brain. Neurogenetics, 1998. 1(4): p. 281-8]. Interestingly, the hypothalamus and the mesencephalon are two areas that show functional sex differences [Reisert, I., E. Kuppers, and C. Pilgrim, Sexual differentiation of central catecholamine systems, in Phylogeny and Development of Catecholamine Systems in the CNS of Vertebrates, W. Smeets and A. Reiner, Editors. 1994, Cambridge University Press: Cambridge. p. 453-462; Vadasz, C., G. Kobor, P. Kabai, I. Sziraki, I. Vadasz, and A. Lajtha, Peiinatal anti-androgen treatment and genotype affect the mesotelencephalic dopamine system and behavior in mice. Horm Behav, 1988. 22(4): p. 528-39]. A more comprehensive profile of Sry expression was described using mouse brains as early as embryonic day 11 (E11) through adulthood (postnatal day 90 or P90) [Mayer, A., G. Mosler, W. Just, C. Pilgrim, and I. Reisert, Developmental profile of Sry transcripts in mouse brain. Neurogenetics, 2000. 3(1): p. 25-30]. For all embryonic stages studies, whole brains were obtained for analysis while at postnatal stages, brain regions such as midbrain, diencephalon, and cortex, were isolated. Sry expression was seen at all stages and in all regions so obtained. Particular emphasis was placed on the detection of linear versus circular Sry transcripts in this study [Gonzalez-Hernandez, T. and M. Rodriguez, Compartmental organization and chemical profile of dopaminergic and GABAergic neurons in the substantia nigra of the rat. J Comp Neurol, 2000. 421(1): p. 107-35]. During E11 through E19, Sry transcripts were found to be in the circular untranslatable form. In contrast, postnatal brain Sry transcripts were found to be in the linear (translatable) form suggesting that Sry in the brain is developmentally regulated. This switch in transcript form is directly opposite to the one observed for the gonads. All the expression studies of Sry have been performed by RT-PCR so far, which raises two concerns: (1) since Sry is a single exon gene expressed at low levels, the RT-PCR data are often difficult to interpret, and (2) RT-PCR studies do not provide specific anatomical localization of expression. Further approaches involving in situ hybridization and immunohistochemistry are needed to confirm specific expression of Sry in the adult brain.

The substantia nigra (SN) is a nucleus located in the midbrain that plays a pivotal role in the control of voluntary movement. The SN is cytoarchitecturally divided into three different parts: the SN pars compacta (SNc), the SN pars reticulata, and the SN pars lateralis [Olanow, C. W. and W. G. Tatton, Etiology and pathogenesis of Parkinson's disease. Annu Rev Neurosci, 1999. 22: p. 123-44]. The SNc, a region rich in dopaminergic neurons, has been associated with a prominent human neurological disorder, Parkinson's disease, as dopaminergic neurons of the SNc preferentially degenerate in Parkinson's patients [Castillo, S. O., J. S. Baffi, M. Palkovits, D. S. Goldstein, I. J. Kopin, J. Witta, M. A. Magnuson, and V. M. Nikodem, Dopamine biosynthesis is selectively abolished in substantia nigra/ventral tegmental area but not in hypothalamic neurons in mice with targeted disruption of the Nurr1 gene. Mol Cell Neurosci, 1998. 11(1-2): p. 36-46]. Parkinson's disease is a neurodegenerative disorder caused by SNc dopaminergic cell death and characterized by rigidity, rest tremor, postural instability and bradykinesia. Dopaminergic neurons of the SNc regulate motor function via nigrostriatal projections to the dorsolateral striatum. Transcriptional factors such as β-catenin, Nurr1 and Pitx3 control the differentiation of the DA phenotype [Maxwell, S. L., H. Y. Ho, E. Kuehner, S. Zhao, and M. Li, Pitx3 regulates tyrosine hydroxylase expression in the substantia nigra and identifies a subgroup of mesencephalic dopaminergic progenitor neurons during mouse development. Dev Biol, 2005. 282(2): p. 467-79; Malbon, C. C., Frizzleds: new members of the superfamily of G-protein-coupled receptors. Front Biosci, 2004. 9: p. 1048-58].

Wnts are secreted, lipid anchored proteins [Nusse, R., Wnts and Hedgehogs: lipid-modified proteins and similarities in signaling mechanisms at the cell surface. Development, 2003. 130(22): p. 5297-305] that bind and activate the Frizzled receptor family [Moon, R. T., A. D. Kohn, G. V. De Ferrari, and A. Kaykas, WNT and beta-catenin signalling: diseases and therapies. Nat Rev Genet, 2004. 5(9): p. 691-701]. In the absence of Wnts, β-catenin is phosphorylated by a destruction protein complex including glycogen synthase kinase-GSK3 β, targeting it for ubiquitination and degradation [Zigova, T., A. E. Willing, E. M. Tedesco, C. V. Borlongan, S. Saporta, G. L. Snable, and P. R. Sanberg, Lithium chloride induces the expression of tyrosine hydroxylase in hNT neurons. Exp Neurol, 1999. 157(2): p. 251-8]. Upon Wnt binding to Frizzled receptors, GSK3 β is inhibited, leading to decreased β-catenin phosphorylation (i.e. stabilisation of β-catenin) and accumulation of stabilised β-catenin in the nucleus, where it modulates transcription of TCF/LEF 1 target genes. Lithium chloride (LiCl) treatment of NT2N neurons at therapeutic doses increased the proportion of tyrosine hydroxylase (TH)-positive neurons by six fold after 5 days in culture [Stambolic, V., L. Ruel, and J. R. Woodgett, Lithium inhibits glycogen synthase kinase-3 activity and mimics wingless signalling in intact cells. Curr Biol, 1996. 6(12): p. 1664-8]. LiCl inhibits GSK3 β and thereby stabilises β-catenin [Castelo-Branco, G., N. Rawal, and E. Arenas, GSK-3beta inhibition/beta-catenin stabilization in ventral midbrain precursors increases differentiation into dopamine neurons. J Cell Sci, 2004. 117(Pt 24): p. 5731-7]. In one study, specific inhibitors of GSK3 β increased the size of the DA population ventral mesencephalon neuron cultures by promoting conversion of Nurr1-expressing precursor neurons in TH-positive DA neurons [Becker, J. B., Gender differences in dopaminergic function in striatum and nucleus accumbens. Pharmacol Biochem Behav, 1999. 64(4): p. 803-12]. Therefore mechanisms that lead to stabilisation of β-catenin provide a potential avenue of drug discovery.

Many gender differences in the function of the SNc and its striatal projections have been described and are well summarized by Becker [Saunders-Pullman, R., Estrogens and Parkinson disease: neuroprotective, symptomatic, neither, or both? Endocrine, 2003. 21(1): p. 81-7]. The clinical implications of these differences are apparent in the onset and progression of Parkinson's disease. Males are more susceptible to Parkinson's disease than females, and epidemiologic studies have suggested a role for estrogens in modulating Parkinson's disease (reviewed in [Sherwin, B. B., Estrogen effects on cognition in menopausal women. Neurology, 1997. 48(5 Suppl 7): p. $S^21^{-6}$]). Estrogen administration lowers the severity of Parkinson's disease symptoms in postmenopausal women with early onset of the disease [Fernandez-Ruiz, J. J., M. L. Hernandez, R. de Miguel, and J. A. Ramos, Nigrostriatal and mesolimbic dopaminergic activities were modified throughout the ovarian cycle of female rats. J Neural Transm Gen Sect, 1991. 85(3): p. 223-9]. In animal models, estrogens dramatically alter the function of dopaminergic cells. For example, rat TH and dopamine turnover rate are higher during diestrus (rising estrogen level) than in estrus (low estrogen level) [Ivanova, T. and C. Beyer, Estrogen regulates tyrosine hydroxylase expression in the neonate mouse midbrain. J Neurobiol, 2003. 54(4): p. 638-47]. Estrogen was also shown to regulate TH expression in the mouse midbrain dopaminergic neurons [Dluzen, D., K. Disshon, and J. McDermott, Estrogen as a modulator of striatal dopaminergic neurotoxicity, in Advances in neurodegenerative disorders, Vol. 1, Parkinson's disease, M. J and T. H, Editors. 1998, Prominent: Scottsdale, Ariz.]. Estrogen also has a protective effect against MPTP-induced neurotoxicity in mice [Serova, L. I., S. Mahaijan, A. Huang, D. Sun, G. Kaley, and E. L. Sabban, Response of tyrosine hydroxylase and GTP cyclohydrolase I gene expression to estrogen in brain catecholaminergic regions varies with mode of administration. Brain Res, 2004. 1015(1-2): p. 1-8]. The specific mechanisms by which estrogens act upon dopaminergic neurons are still poorly understood. Short-term injection of estradiol benzoate in rats increased TH mRNA levels in dopaminergic neurons of the SNc, but long-term administration did not [Leranth, C., R. H. Roth, J. D. Elsworth, F. Naftolin, T. L. Horvath, and D. E. Redmond, Jr., Estrogen is essential for maintaining nigrostriatal dopamine neurons in primates: implications for Parkinson's disease and memory. J Neurosci, 2000. 20(23): p. 8604-9]. Consistently, in primates, short-term ovariectomy (10 days) decreased the number of TH-positive cells in the SNc, a reversible effect, whereas long-term ovariectomy (30 days) results in a permanent loss the SNc dopamine cells [Maharjan, S., L. Serova, and E. L. Sabban, Transcriptional regulation of tyrosine hydroxylase by estrogen: opposite effects with estrogen receptors alpha and beta and interactions with cyclic AMP. J Neurochem, 2005. 93(6): p. 1502-14]. The actual transcriptional regulation of TH by estrogen is complex and poorly known, and it seems to depend on the type of estrogen receptors: estrogen increases TH activity with ERalpha but decreases it with ER beta [Castner, S. A., L. Xiao, and J. B. Becker, Sex differences in striatal dopamine: in vivo microdialysis and behavioral studies. Brain Res, 1993. 610 (1): p. 127-34]. In addition, there are sex differences in the response of estrogen, as effects seen in females on striatal dopamine release are not seen in males [Dluzen, D. E. and J. L. McDermott, Developmental and genetic influences upon gender differences in methamphetamine-induced nigrostriatal dopaminergic neurotoxicity. Ann N Y Acad Sci, 2004. 1025: p. 205-20], and estrogen functions as a neuroprotectant against metamphetamine in females, but not in males [Canuth, L. L., I. Reisert, and A. P. Arnold, *Sex chromosome genes directly affect brain sexual differentiation*. Nat Neurosci, 2002. 5(10): p. 9933-4]. More generally, genetically modified mouse models have shown a sex chromosome effect on the number of TH-positive cells cultured from embryonic mesencephalon [Kumer, S. C. and K. E. Vrana, Intricate regulation of tyrosine hydroxylase activity and gene expression. J Neurochem, 1996. 67(2): p. 443-62], suggesting a complex regulation of TH not limited to endocrine influences. In fact, modulation of TH is complex and involves transcriptional control, alternative RNA processing and regulation of RNA stability [Abramham, I. et al., Increased PKA and PKC activities accompany neuronal differentiation of NT2/D1 cells. J. Neurosci. Res., 1991. 28: p. 29 39].

It is proposed that sex differences in the molecular characteristics of brain regions and their associated behaviour are influenced by genetic factors independently of gonadal hormones. The present inventors propose a role for the Y-chromosome encoded testis-determining factor Sry as a transcriptional regulator to increase TH production in DA neurons of the male SN in rodents and humans, and describe a role for Sry in Parkinson's disease.

SUMMARY OF THE INVENTION

The present inventors have developed a method for treating or preventing Parkinson's disease in a patient by administering to the patient neuronal cells which express sex determining protein (SRY).

In a first aspect of the present invention there is provided an isolated neuronal cell transformed with a nucleic acid encoding SRY, wherein the transformed cell expresses SRY.

In a second aspect of the present invention there is provided a population of neuronal cells transformed with a nucleic acid molecule encoding SRY, wherein the transformed cells express SRY.

In a third aspect of the present invention there is provided a method for treating or preventing Parkinson's disease in a patient, the method comprising administering to the patient a therapeutically effective population of neuronal cells transformed with a nucleic acid molecule encoding SRY, wherein the transformed cells express SRY.

These and other objects, advantages, and features of the invention will become apparent to those persons skilled in the art upon reading the details of the cells, cell population and methods as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
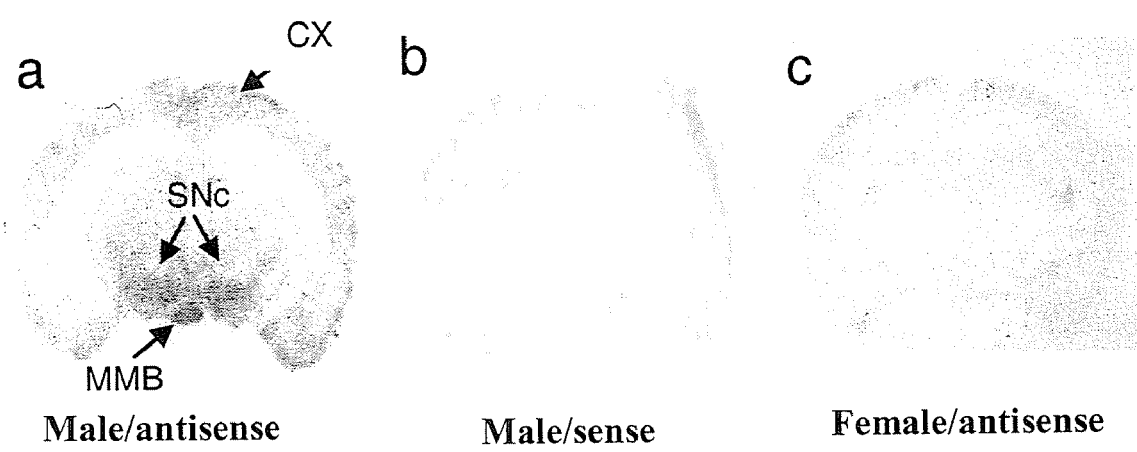
FIG. 1 shows radioactive in situ hybridization on adult mouse brains using an Sry mouse probe of approximately 500 bp in the (a) medial medullary body, (b) the substantia nigra, and (c) the cortex.

Before the present cells, cell population and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a molecule" or "a protein" includes a plurality of such molecules or proteins and reference to "the promoter" includes reference to one or more promoters and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present inventors have developed a method for treating or preventing Parkinson's disease in a patient by administering to the patient a population of neuronal cells encoding sex determining protein (SRY).

In a first aspect there is provided an isolated neuronal cell transformed with a nucleic acid encoding SRY, wherein the transformed cell expresses SRY.

In a second aspect of the present invention there is provided a population of neuronal cells transformed with a nucleic acid molecule encoding SRY, wherein the transformed cells express SRY.

In a preferred embodiment of the present invention the population of neuronal cells comprise at least 95%, preferably at least 96%, more preferably at least 97%, 98%, 99% or substantially pure, stable, post-mitotic human NT2N neurons.

In another preferred embodiment of the present invention, the nucleic acid molecule encoding SRY is under the control of a heterologous promoter.

The term "heterologous promoter" as used herein means a promoter other than the promoter normally used to control SRY gene expression in a cell.

The amino acid (SEQ ID No. 2) and nucleic acid (SEQ ID No. 2) sequences for SRY are as follows:

```
  1 M   Q   S   Y   A   S   A   M   L   S   V   F   N   S   D   D   Y   S   P   A    20
  1 ATGCAATCATATGCTTCTGCTATGTTAAGCGTATTCAACAGCGATGATTACAGTCCAGCT                      60

21 V   Q   E   N   I   P   A   L   R   R   S   S   S   F   L   C   T   E   S   C    40
 61 GTGCAAGAGAATATTCCCGCTCTCCGGAGAAGCTCTTCCTTCCTTTGCACTGAAAGCTGT                     120

41 N   S   K   Y   Q   C   E   T   G   E   N   S   K   G   N   V   Q   D   R   V    60
121 AACTCTAAGTATCAGTGTGAAACGGGAGAAAACAGTAAAGGCAACGTCCAGGATAGAGTG                     180

61 K   R   P   M   N   A   F   I   V   W   S   R   D   Q   R   R   K   M   A   L    80
181 AAGCGACCCATGAACGCATTCATCGTGTGGTCTCGCGATCACAGGCGCAAGATGGCTCTA                     240

81 E   N   P   R   M   R   N   S   E   I   S   K   Q   L   G   Y   Q   W   K   M   100
241 GAGAATCCCAGAATGCGAAACTCAGAGATCAGCAAGCAGCTGGGATACCAGTGGAAAATG                     300
```

```
101 L   T   E   A   E   K   W   P   F   F   Q   E   A   Q   K   L   Q   A   M   H   120

301 CTTACTGAAGCCGAAAAATGGCCATTCTTCCAGGAGGCACAGAAATTACAGCCCATGCAC 360

121 R   E   K   Y   P   N   Y   K   Y   R   P   R   R   K   A   K   M   L   P   K   140

361 AGAGAGAAATACCCGAATTATAAGTATCGACCTCGTCGGAAGGCGAAGATGCTGCCGAAG 420

141 N   C   S   L   L   P   A   D   P   A   S   V   L   C   S   E   V   Q   L   D   160

421 AATTGCAGTTTGCTTCCCGCAGATCCCGCTTCGGTACTCTGCAGCGAAGTGCAACTGGAC 480

161 N   R   L   Y   R   D   D   C   T   K   A   T   H   S   R   M   E   H   Q   L   180

481 AACAGGTTGTACAGGGATGACTGTACGAAAGCCACACACTCAAGAATGGAGCACCAGCTA 540

181 G   H   L   P   P   I   N   A   A   S   S   P   Q   Q   R   D   R   Y   S   H   200

541 GGCCACTTACCGCCCATCAACGCAGCCAGCTCACCGCAGCAACGGGACCGCTACAGCCAC 600

201 W   T   K   L   *                                                   205

601 TGGACAAAGCTGTAG                                                     615
```

In a third aspect of the present invention there is provided a method for treating or preventing Parkinson's disease in a patient, the method comprising administering to the patient a therapeutically effective population of neuronal cells transformed with a nucleic acid molecule encoding SRY, wherein the transformed cells express SRY.

In a preferred embodiment of the present invention the population of neuronal cells are injected into the brain of the patient. In a particularly preferred embodiment, the population of neuronal cells is injected into the region surrounding the substantia nigra, or injected into the substantia nigra itself.

As used herein, the term "therapeutically effective population" means a population of neuronal cells expressing SRY sufficient to treat or ameliorate the symptoms of Parkinson's disease.

As used herein, the term "population" in the context of the present invention refers to one or more cells. According to the present invention, a population from a culture of a substantially pure, stable, homogenous sample of post-mitotic neurons is administered to either a non-human animal or a human. Accordingly, the method of the present invention relates to the administration of one or more cells from a culture of a substantially pure, stable, homogenous sample of post-mitotic neurons into the brain of either a non-human animal or human.

In a preferred embodiment of the present invention, transfected NT2N neuron cells expressing SRY are produced by the method described in Example 1 for obtaining >95% pure post-mitotic human neurons (termed NT2N cells) from a human teratocarcinoma cell line (termed NTera2/clone D1 or NT2 cells); following treatment of the NT2 cells with retinoic acid (RA). The stable, homogeneous population of pure human neurons may then be implanted in vivo into the brains of individuals suffering from CNS diseases or disorders such as Parkinson's disease.

The administration of NT2N cells to the brain of an individual is known from U.S. Pat. No. 7,011,827, which is incorporated herein by reference. The invention disclosed in U.S. Pat. No. 7,011,827 relates to a method of treating an individual suffering from a brain injury as a result of stroke and comprises administering a sample of human NT2N neurons at or near a site of injury such that integration of the cells within the brain promotes axonal regeneration and ameliorates the stroke injury.

The NT2 cell line is unique among all other teratocarcinoma cell lines that are capable of differentiating into neurons, glia and mesenchymal cells, because the NT2 cells appear to correspond to progenitor cells, the progeny of which are restricted to the neuronal lineage [Andrews, P. W., et al., The expression of MHC antigens by human tetracarcinoma derived cell lines. Tissue Antigens, 1981. 17: p. 493 500; Andrews, P. W. et al., Pluripotent embryonal carcinoma clones derived from the human tetracarcinoma cell line Tera-2, Lab. Invest. 1984. 50: p. 147 162; Andrews, P. W, Retinoic acid induces neuronal differentiation of a cloned human embryonal carcinoma cell line in vitro, Devel. Biol. 1987. 103: p. 285 293; Kleppner, S. R., et al., Long-term survival and maturation of neurons derived from the human cell line N-tera 2 after transplantation into nude mice brain, Soc. Neurosci. Abst. 1992. 18: p. 782; Lee, V. M.-Y. and P. W. Andrews, Differentiation of NTERA-2 clonal human embryonal carcinoma cells into neurons involves the induction of all three neurofilament proteins, J. Neurosci. 1986. 6: p. 514 521; Younkin, D. P. et al., Inducible expression of neuronal glutamate receptor channels in the NT2 human cell line, Proc. Natl. Acad. Sci. U.S.A. 1993. 90: p. 2174 2178; Pleasure, S. J., et al., Pure, postmitotic, polarized human neurons derived from NTera 2 cells provide a system for expressing exogenous proteins in terminally differentiated neurons, J. Neurosci. 1992. 12: p. 1802 1815]. Further characterization of the NT2N cells has shown that these cells most closely resemble CNS neurons [Backlund, E.-O. et al., Transplantation of adrenal medullary tissue to striatum in parkinsonism, J. Neurosurg. 1985. 62: p. 169 173]. The NT2N cells exhibit other interesting properties of CNS neurons, i.e. they express almost exclusively the 695 amino acid long amyloid precursor protein (APP), produce and secrete the β-amyloid or A4 (β/A4) peptide found in Alzheimer's disease amyloid plaques and bear glutamate receptor channels on their cell surface.

The NT2N neurons used in the present invention are preferably transfected with a nucleic acid molecule encoding SRY prior to induction or differentiation.

As used herein the term "nucleic acid molecule" refers to genomic DNA, cDNA, synthetic DNA and RNA, mRNA and antisense DNA and RNA which is introduced into the cell or an ancestor cell. The nucleic acid molecule is preferably provided in an expression vector which includes the coding region of SRY whose production by cells is desired, operably linked to essential regulatory sequences such that when the vector is transfected into the cell, the nucleic acid molecule is capable of being expressed within the cell.

Expression vectors that encode nucleic acid molecules comprise a nucleotide sequence that encodes a protein to be produced operably linked to regulatory elements needed for gene expression. Accordingly, incorporation of the DNA or RNA molecule into the neuron cell results in the expression of the DNA or RNA encoding the protein and thus, production of the protein.

The nucleic acid molecule that includes the nucleotide sequence encoding the protein operably linked to the regulatory elements may remain present in the cell as a functioning episomal molecule or it may integrate into the cell's chromosomal DNA. The nucleic acid molecules may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule.

The necessary elements of an expression vector include a nucleotide sequence that encodes a protein and the regulatory elements necessary for expression of that sequence in the cells. The regulatory elements are operably linked to the nucleotide sequence that encodes the protein to enable expression. The nucleotide sequence that encodes the protein may be cDNA, genomic DNA, synthesized DNA or a hybrid thereof or an RNA molecule such as mRNA.

The regulatory elements necessary for gene expression include: a promoter, an initiation codon, a stop codon, and a polyadenylation signal. It is necessary that these elements be operable in the neurons. Moreover, it is necessary that these elements be operably linked to the nucleotide sequence that encodes the protein such that the nucleotide sequence can be expressed in the neuron cells and thus the protein can be produced.

Initiation codons and stop codon are generally considered to be part of a nucleotide sequence that encodes the protein. However, it is necessary that these elements are functional in the neurons. Similarly, promoters and polyadenylation signals used must be functional within the neuron cells. Examples of promoters useful to practice the present invention include but are not limited to cytomegalovirus promoter, particular the immediate early promoter, SV40 promoter and retroviral promoters. Examples of polyadenylation signals include, but are not limited, to SV40 polyadenylation signal.

In order for nucleic acid molecule in an expression vector to be expressed, the regulatory elements must be operably linked to the nucleotide sequence that encodes the protein. Accordingly, it is necessary for the promoter and polyadenylation signal to be in frame with the coding sequence. In order to maximize protein production, regulatory sequences may be selected which are well suited for gene expression in the neuronal cells. Moreover, codons may be selected which are most efficiently transcribed in the cell. One having ordinary skill in the art can produce nucleic acid molecules as expression vectors which are functional in neurons.

In a preferred embodiment of the present invention $1\times10^3$ to $1\times10^6$ neurons are implanted. Two techniques have been used for neural transplantation, the first comprises stereotaxic surgery in which a neuron cell suspension is implanted into the brain, the second in which the cells are grafted into the brain by microsurgery. Techniques for transplanting neural tissue have been described [Lindvall, O. et al., Transplantation in Parkinson's disease: two cases of adrenal medullary grafts to the putamen, Ann. Neurol. 1987. 22: p. 457 468; Madrazo, I. et al., Open microsurgical autograft of adrenal medulla to the right caudate nucleus in two patients with intractable Parkinson's disease, New Engl. J. Med. 1987. 316: p. 831 834; Dewing, P., C. W. Chiang, K. Sinchak, H. Sim, P. O. Fernagut, S. Kelly, M. F. Chesselet, P. E. Micevych, K. H. Albrecht, V. R. Harley, and E. Vilain, *Direct regulation of adult brain function by the male-specific factor SRY*. Curr Biol, 2006. 16(4): p. 415-20] and are incorporated herein by reference.

Neurons may be transplanted into the brains of non-human animals by injection of neurons into one hemisphere using a stereotaxic instrument and a handheld 10 μl Hamilton syringe.

In order that the nature of the present invention may be more clearly understood, preferred forms thereof will now be described with reference to the following non-limiting examples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Methods and Materials

Generation and Transfection of NT2 Neurons

Undifferentiated NT2 cells were subcultured at $1\times10^6$ cells per 78 cm2 flask. After cells were allowed to adhere overnight, fresh DMEM/F12 medium (Gibco) containing $10^{-6}$ M retinoic acid was added. Every 2 days, medium was replaced. Following 7 days RA treatment, cells were replated (1:6) and transfected with an SRY-expression plasmid using JetPei (PolyPlus trasnsfections) or Fugene6 (Roche) transfection reagent. 2 days after transfection, RA-containing medium was added and replaced every alternate day until 7 days post-transfection. The typical transfection efficiency obtained was between 20-40% which is significantly higher than previous methods. Alternatively, we have optimised the transfection of undifferentiated NT2 cells whereby SRY and GFP cDNA are transfected to a high efficiency (40-60%) and FACS-sorted. We envisage that these sorted cells can be differentiated with RA according the method we outlined above.

6-Hydroxydopamine Lesioning and Transplantation

Pure SRY-transfected NT2 neurons will be transplanted according to the following protocol.

Young adult C57BL/6J mice aged 10-12 weeks were used. Animals were pretreated with desipramine hydrochloride (25 mg/kg, Sigma) to reduce damage to noradrenergic system. Anesthesia was performed by i.p. injection of chloral hydrate (500 mg/kg). Lesions of the right SN were produced by stereotaxic injection of 6-hydroxydopamine hydrobromide (6-OHDA)(Sigma-Aldrich Pty Ltd, Castle Hill, Australia). Briefly, a 2 ml of 6-OHDA solution (5 mg ml-1,6-OHDA in 0.9% normal saline with 0.02% ascorbic acid) were deposited at the following coordinates: AP mm, L mm and vertical mm with respect to bregma.

3 weeks after lesioning animals were subjected to behavioural studies as described. The next day selected animals were anaesthetized and mounted in stereotacetic frame. A hole sufficient to allow glass cannula with external diameter of 1 mm was drilled at the same coordinates as above. First, blunt cannula was introduced above right SN and left in place for 4 min. It was replaced by cannula containing SRY-transfected NT2N cells and connected to 100 μl Hamilton syringe mounted in a syringe pump (Cole-Parmer, Vernon Hills, Ill., USA). The cell suspension was injected at a rate of 0.7 ml/hr. Cannula was left in place for additional 4 min before being slowly withdrawn. Histological evidence of SN area distortion by transplantation cannula was set as exclusion criteria from further analyses.

Rotational Behaviour Assessment

The asymmetty of striatal innervation following 6-OHDA was assessed by amphetamine (5 mg/kg) induced rotatory response. Animals were tested at 3 weeks after lesioning and at 4, 8, 12 and 20 weeks following transplantation. Rotatory response was recorded for 90 min commencing from amphetamine injection. The net number of turns (right minus left) was counted by observer blinded to subject identity. In preliminary experiments we established that animals displaying >500 turns/90 min at 3 weeks after lesioning maintained stable rotatory response on subsequent amphetamine challenges. Accordingly, it was set as a selection criterion for transplantation, allowing assessment of potential behavioural improvement.

Immunohistochemistry

Experimental animals were sacrificed 2 weeks to one month after last behavioural trial to allow restoration of DAT expression in dopaminergic terminals (ref. PNAS). Briefly, animals were killed by an overdose of sodium pentobarbitone (lethobarb; 0.35 mg/gm) and perfused with warmed saline followed by 4% paraformaldehyde. Coronal sections (16 μm thick) were made through the striatum and collected at a 1:15 series. Series of 1:3 coronal sections (25 μm thick) were cut through the SN and mounted onto gelatin-coated slides. The primary antibodies used were: rat anti-DAT (Chemicon, Temecula, Calif., 1:3000 in PBS, 0.3% triton X-100 and 1.0% normal rabbit serum), anti-TH (Sigma), anti-NeuN and other neuronal markers. Fluorescent Alexa-dye secondary antibodies were used to visualised the location of the transplanted cells.

Stereological Methods

The localization of the oculomotor nerve rootlets was the criteria for delineating SN from VTA. VTA was considered to be within and medial to the rootlets, whereas SN was considered to be located laterally. Outlines of normal SN were generated by means of Stereo Investigator Program, and superimposed on index sections to obtain upper limit of lesioned SN or area of SNpc, oriented according to structures such as hippocampus and ventricles. Absolute number of TH-ve cells within delineated area was obtained from every section in series containing SN (normally 5-6 sections). Counts were derived by means of meander scan function of Stereo Investigator Program which moved consecutively counting field through the entire delineated area. Sections were examined under x63 oil lens; only cells with clearly labeled TH-ve cell bodies and neutral red counterstained nuclei were counted. The index of striatal DA innervation was estimated, derived by dividing striatal DAT density by the number of TH-ve cells in SN.

Example 2

Results

Expression of SRY RNA in the Brain

In situ hybridization on adult mouse brains was performed using an SRY mouse probe of approximately 500 base pairs in length. SRY expression was clearly localized to three main areas in the adult male brain: the medial mammillary body, substantia nigra, and scattered throughout the cortex (FIG. 1). The results were confirmed using a SRY-EGFP (Enhanced Green Fluorescent Protein) generated transgenic mouse in which EGFP expression is driven by 7.5 kb of the SRY promoter.

Preparation of Mouse SRY Antibody

Further confirmation of significant expression of SRY in specific regions of the mouse adult brain was provided by immunohistochemistry using antibodies raised against SRY protein. Antibodies against mouse SRY were generated in rabbits using a peptide which corresponds to amino acids 88-120 of the mouse SRY protein [Pompolo, S. and V. R. Harley, Localisation of the SRY-related HMG box protein, SOX9, in rodent brain. Brain Res, 2001. 906(1-2): p. 143-8]. SRY antibodies were affinity-purified from rabbit serum [Pompolo, S. and V. R. Harley, Localisation of the SRY-related HMG box protein, SOX9, in rodent brain. Brain Res, 2001. 906(1-2): p. 143-8]. Antibody-specificity was demonstrated using SRY-transfected COS7 cells and protocols were further optimized using mouse gonadal ridges (data not shown) before use on brain sections with purified pre-immune sera as a negative control.

Expression of SRY Protein in the Brain

Figure 2:
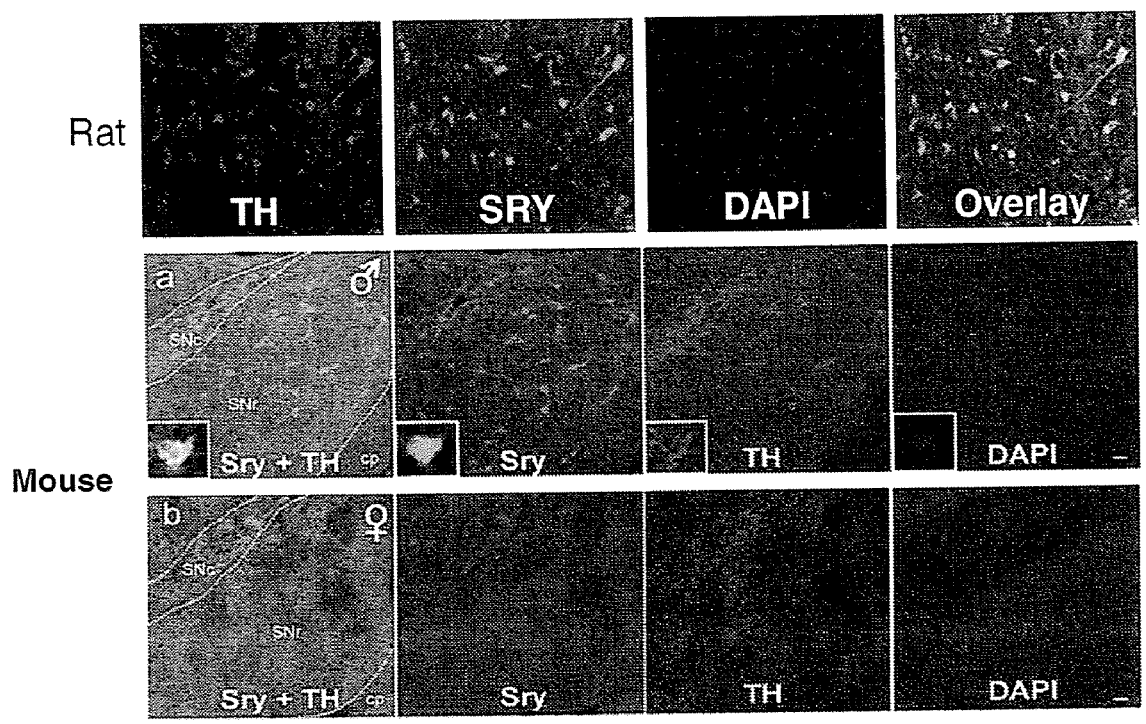
FIG. 2 shows cellular localization of SRY in the adult rat and male mouse SNc indicated by enhanced green fluorescent protein (EGFP) expression in a Sry-EGFP transgenic mice in which EFGP expression is driven by 7.5 kb of the Sry promoter.

SRY protein expression in the SNc of adult male brains by immunohistochemistry was examined. SRY protein was observed in all regions of the SNc, with most SRY-positive cells in the pars compacta region of the SNc of both mouse and rat (FIG. 2). SRY staining was stronger in the nucleus than in the cytoplasm of cells. The nucleus is the presumed site of action of SRY as a DNA-binding transcription factor. Given that the staining pattern of SRY closely resembles that of neurons in the SNc, double labelling was performed with a neuronal marker (tyrosine hydroxylase, TH; FIG. 2) and cells counted. Of the total population of (DAPI-stained) cells, ten percent were SRY-positive. All SRY-positive cells were also TH-positive neurons. These results demonstrate that SRY protein is produced in the adult male mouse and rat SNc, where it is localized exclusively in TH-positive neurons.

SRY Protein in Human SN

Figure 3:
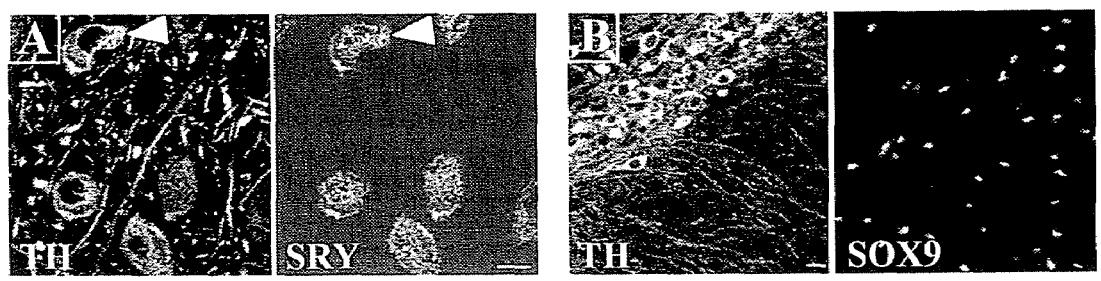
FIG. 3 shows SRY expression in the substantia nigra of human adult brains by immunohistochemistry using an antibody to SRY. (A) human adult male SN, SRY protein (▶) localized to the cytoplasm and nuclei of TH+ neurons; (B) unlike SRY which is expressed in TH+ neurons, SOX9 is localized in the nuclei of other cell populations within the SN, possibly in glial cells. Scale bar, 20 μm.

SRY expression in the SN of human adult male brains by immunohistochemistry was examined using human SRY antibody. SRY was detected in all regions of the SN, localized in both nuclei and cytoplasm of TH+ neuronal cells, consistent with our rodent data ([Pompolo, S. and V. R. Harley, Localisation of the SRY-related HMG box protein, SOX9, in rodent brain. Brain Res, 2001. 906(1-2): p. 143-8]; FIG. 3A). All SRY+ cells were TH+. The inventors had previously observed SOX9 expression in the glial cells in the cerebellum of mouse brains [Landgraf, R., Antisense targeting in behavioural neuroendocrinology. J Endocrinol, 1996. 151(3): p. 333-40]. The inventors show here that in the male SNc SOX9 is not localized in TH+ cells, implying that SRY regulates different target genes in the brain than in the gonad (FIG. 3B).

Figure 4:
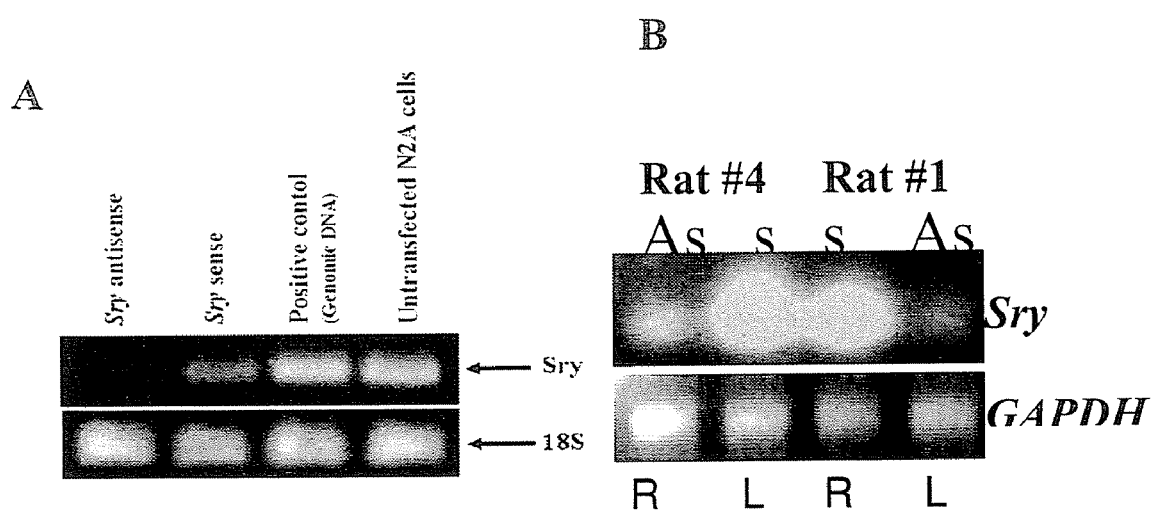
FIG. 4 shows that Sry antisense oligodeoxynucleotides (ODN) down-regulates Sry expression in vitro and in vivo. (A) RT-PCR verifies down-regulation of Sry expression by an ODN antisense in Neuro-2A cultures; (B) RT-PCR demonstrates a decrease in Sry mRNA expression in vivo in two separate rats infused with anti-Sry ODN. R and L represent right and left sides of the rat brain in which either antisense (As) or sense (s) was infused. The sides of the brain in which antisense was infused exhibited less Sry expression compared to sides infused with sense in all cases.

Down-Regulation of SRY In Vivo and In Vitro by Anti-Sense Oligodeoxyynucleotides Prior to infusing cDN into rats, activity of antisense SRY ODN was measured in vitro. Using transfection assays, the inventors show that 5 μg of our antisense SRY ODN cocktail down-regulated expression of endogenous SRY in N2A cells (SRY-expressing cells) by 9 fold, while cells transfected with the sense cocktail showed no down-regulation of SRY (FIG. 4B). Genomic rat DNA and untransfected N2A cells served as positive controls. Down-regulation of SRY expression was also determined in vivo. Rat SN were unilaterally infused (detailed below in research design) with either sense or antisense SRY ODN, and levels of SRY expression in the SNc was determined by RT-PCR after dissection. Consistently, the side in which SRY antisense was infused into the SN of animals for 10 days exhibited considerably less SRY mRNA expression compared to that of the sense infused side (FIG. 4A).

Effects of SRY on TH Neurons in the SNc and Striatum

Figure 5:
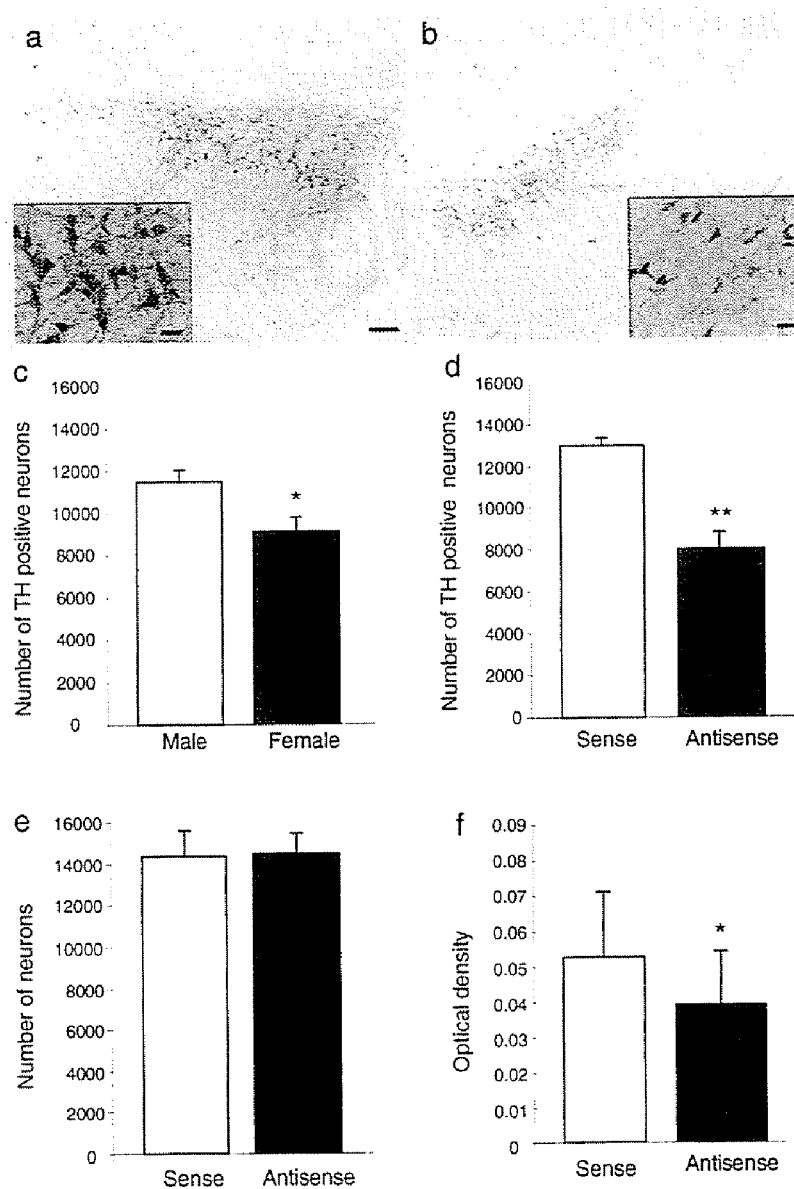
FIG. 5 shows Sry antisense ODN decreases the number of TH+ neurons in the SNc. (a) ipsilateral infusions of Sry sense ODN had no effect on the number of TH-ir neurons and served as an internal control; (b) contralateral infusions of antisense ODN (in the same animal) significantly reduced the number of TH+ neurons in the SNc (inset: 63× magnification); (c) when comparing age-matched wild-type male and female rats, the number of TH-positive neurons in the SNc of females was 20% lower than in males (n=6); (d) infusions of Sry antisense ODN in the SNc of male rats reduced the number of TH-ir neurons by 38% compared to sense ODN infused SNc (n=13); (e) no difference between Sry antisense or sense ODN was observed in the overall number of neurons using Nissl staining (n=13); (f) optical density measured a 26% decrease in striatal TH-ir between sides infused with Sry antisense and sense ODN (n=6). Scale bar, 200 μm and 10 μm (insets).

To investigate the effect of SRY on TH neurons in vivo and consequent motor behavior in rats, SRY was specifically down-regulated in the SNc by an antisense targeting method [Vadasz, C., H. Baker, S. J. Fink, and D. J. Reis, *Genetic effects and sexual dimorphism in tyrosine hydroxylase activity in two mouse strains and their reciprocal F1 hybrids.* J Neurogenet, 1985. 2(3): p. 219-30]. Before evaluating the role of SRY function in the SNc, the inventors first tested whether the number of TH neurons was sexually dimorphic in the rat SNc. In females, the number of TH-immunoreactive (TH-ir) neurons was reduced by 20% compared to their age-matched male controls (FIG. 5c, P=0.032; n=6). This suggests that the expression of TH, the rate-limiting enzyme of the dopaminergic pathway, is sexually dimorphic in rats, which correlates with similar findings in mice [Gundersen, H. J., P. Bagger, T. F. Bendtsen, S. M. Evans, L. Korbo, N. Marcussen, A. Moller, K. Nielsen, J. R. Nyengaard, B. Pakkenberg, and et al., *The new stereological tools: disector, fractionator, nucleator and point sampled intercepts and their use in pathological research and diagnosis.* Apmis, 1988. 96(10): p. 857-81]. Subsequently, SRY antisense ODN was microinfused into one side of male rat SNcs. As a control, the contralateral SNcs were infused with SRY sense ODN. This design produced a within-subject control that allowed for direct comparison of the effects of sense and antisense ODN treatments. Infusion of SRY antisense ODN into the SN reduced the number of TH-ir neurons by 38% when compared to the number of TH-ir neurons in the side infused with SRY sense ODN, as quantified using an optical fractionator sampling design [Whishaw, I. Q., N. C. Woodward, E. Miklyaeva, and S. M. Pellis, Analysis of limb use by control rats and unilateral DA-depleted rats in the Montoya staircase test: movements, impairments and compensatory strategies. Behav Brain Res, 1997. 89(1-2): p. 167-77] (FIGS. 5a,b,d, P=0.0022, n=13). Higher magnification and quantification indicates that neural degeneration in TH-positive cells has not occurred (FIG. 5b inset). Adjacent coronal brain sections stained with thionin (Nissl staining) revealed no difference in the number of cells resembling neurons between treated and untreated SNcs (FIG. 5e). Furthermore, females treated with SRY antisense ODN on one side and SRY sense ODN on the other displayed no difference in number of SNc TH-ir neurons (data not shown) suggesting that the SRY antisense cocktail used in this study was specific for the SRY gene. Taken altogether, these results suggest that the reduction of TH-positive neurons was due to a reduction in TH expression and not a result of the loss of TH-ir neurons. TH neurons in the SNc project to the striatum providing dopamine innervation. Thus the inventors tested whether SRY antisense ODN infusions in the SNc altered TH immunostaining in the striatum.

Quantification of striatal TH-ir by optical density demonstrated that TH was decreased by 26% in the striatum, which received TH projections from the SRY antisense ODN treated SNc (FIG. 5f, P=0.042, n=6).

SRY Effect on Sensorimotor Function

Figure 6:
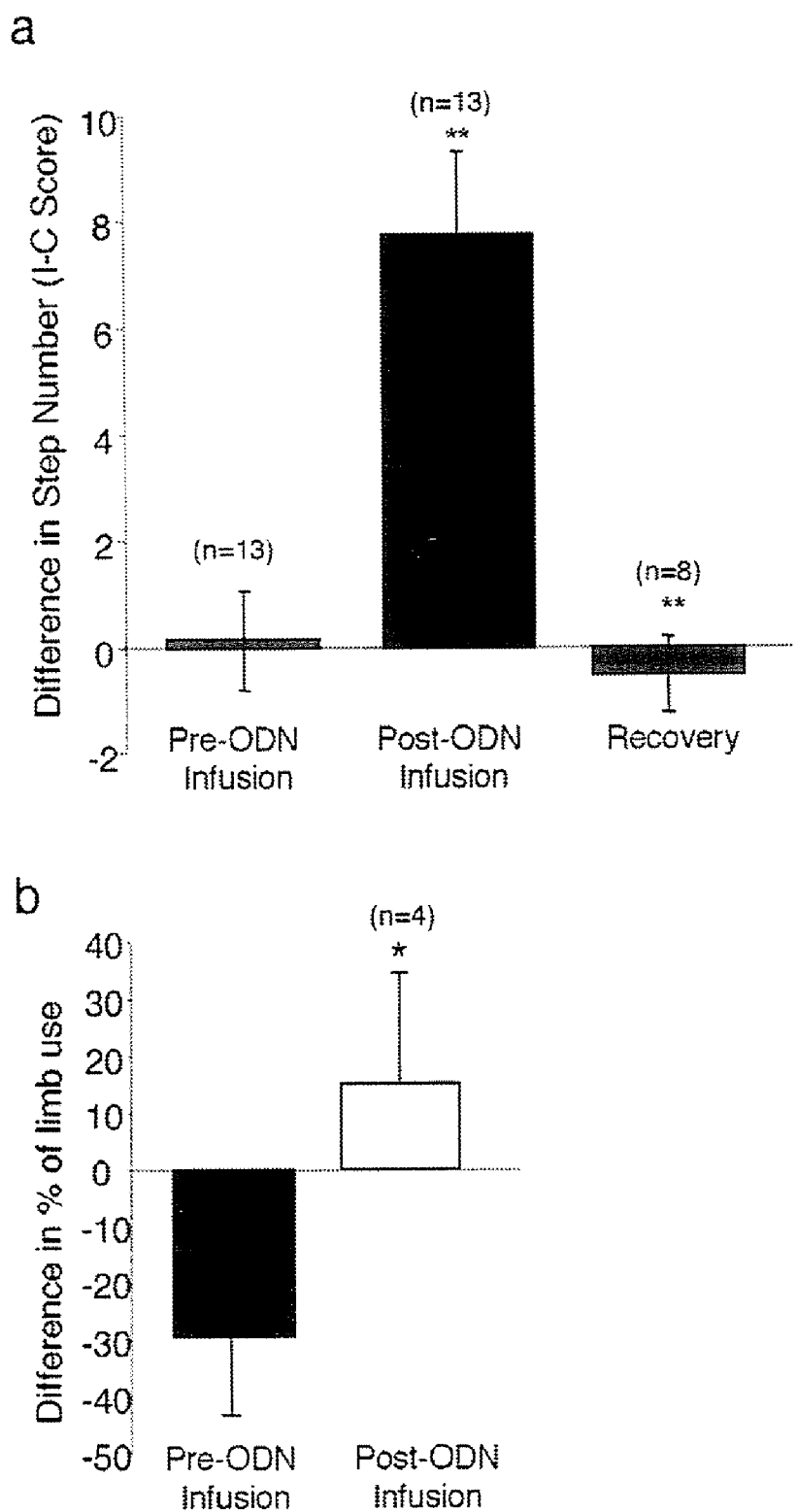
FIG. 6 shows deficits in sensolimotor behaviours induced by Sry down-regulation in the SN. (a) akinesia tests showed a significant decrease in the number of steps taken by the contralateral forelimb in animals infused with Sry antisense ODN. The overall index of akinesia score (I-C) of 0.2 pre-ODN infusion reflects equal usage of both limbs. A positive I-C score of 7.3 observed post-ODN infusion revealed a significant bias for ipsilateral limb use. I-C score returns to baseline 7 days after ODN termination (recovery); (b) limb-use asymmetry test revealed a 35% decrease in limb use after Sry antisense ODN infusions. Animals demonstrated an ipsilateral forelimb bias for usage in cylinder exploration post-Sry antisense ODN infusions as shown by a significant I-C score. Reluctance to contralateral forelimb usage correlates to decrease of TH-positive neurons in the SN. I-C is a single overall score which is obtained by subtracting the use value of contralateral limb from ipsilateral limb.

Since a decrease in dopamine, the product of TH activity, causes quantifiable deficits in sensorimotor function [Schallert, T., S. M. Fleming, J. L. Leasure, J. L. Tillerson, and S. T. Bland, CNS plasticity and assessment of forelimb sensorimotor outcome in unilateral rat models of stroke, cortical ablation, parkinsonism and spinal cord injury. Neuropharmacology, 2000. 39(5): p. 777-87], the effect of SRY antisense ODN on specific motor functions was assessed. The inventors used well-established, reliable, and sensitive behavioral tests, such as the akinesia and limb-use asymmetry tests to assess sensorimotor asymmetries in SRY antisense ODN treated rats [Fleming, S. M., C. Zhu, P. O. Fernagut, A. Mehta, C. D. DiCarlo, R. L. Seaman, and M. F. Chesselet, *Behavioral and immunohistochemical effects of chronic intravenous and subcutaneous infusions of varying doses of rotenone.* Exp Neurol, 2004. 187(2): p. 418-29]. In the akinesia test, animals with dopamine depletions typically take fewer steps with their contralateral forelimbs compared with their ipsilateral forelimbs. When comparing rats before and after SRY antisense ODN infusions, a 50% reduction in the number of steps taken by the contralateral forelimbs was observed, suggesting a behavioral effect of SRY decrease in SNc on the expected, contralateral side. A pre-ODN infusion I-C (ipsilateral minus contralateral) score of 0.2 reflected equal usage of both forelimbs in stepping when individual limbs were examined. However, in post-ODN infusion trials, animals stepped more readily when the ipsilateral limb was isolated, as represented by a significant positive I-C value of 7.3, suggesting a considerable deficit in limb usage (FIG. 6a, P<0.001; n=13). Rats assessed 7 days after termination of ODN treatment recover their baseline motor behaviour (FIG. 6a) and their number of TH+ neurons (not shown). In the limb use asymmetry test (another classically used test of the nigrostriatal pathway), the inventors observed a decrease of 26.4% in the usage of the contralateral limb after infusion of SRY antisense ODN. The negative I-C score during pre-ODN infusion trials (−29.7±13.3) indicated an inherent bias by the animals for favouring their contralateral limb during cylinder exploration. However, the tendency of limb usage switched to significantly favor the ipsilateral limb that was associated with sense ODN treatments during post-ODN trials (FIG. 6b, P=0.013; n=4). Both sets of behaviour tests exhibited the same trend where animals uniformly decreased their contralateral limb usage and began favouring their ipsilateral limbs. These data suggest that SRY down-regulation in the SNc reversibly reduces motor behaviours, which correlates with its effect on TH expression in the nigrostriatal system. Similar reduction of striatal TH induced by other mechanisms has been shown to affect motor behavior without cell loss in the SNc [Andrews, P. W., *Retinoic acid induces neuronal differentiation of a cloned human embryonal carcinoma cell line in vitro.* Dev Biol, 1984. 103(2): p. 285-93].

SRY Expression in NT2N Neurons

The inventors analyzed the role of SRY in TH expression using differentiated NT2N neurons as a cell culture model of DA neurons. NT2 cells are derived from a male human germ cell tumor and consist of precursor cells that differentiate in vitro, after exposure to retinoic acid (RA), into NT2N neurons

[Zigova, T., A. E. Willing, S. Saporta, M. M. Daadi, M. P. McGrogan, T. S. Randall, T. B. Freeman, J. Sanchez-Ramos, and P. R. Sanberg, Apoptosis in cultured hNT neurons. Brain Res Dev Brain Res, 2001. 127(1): p. 63-70]. Depending on the duration of RA exposure, up to 60% of NT2N neurons express TH. NT2Ns have cellular machinery typical of DA neurons as they also express dopamine transporter (DAT), dopamine receptor (D2) and aldehyde dehydrogenase, an enzyme exclusively expressed by ventral mesencephalic DA neurons [Castelo-Branco, G., N. Rawal, and E. Arenas, GSK-3beta inhibition/beta-catenin stabilization in ventral midbrain precursors increases differentiation into dopamine neurons. J Cell Sci, 2004. 117(Pt 24): p. 5731-7; Misiuta, I. E., L. Anderson, M. P. McGrogan, P. R. Sanberg, A. E. Willing, and T. Zigova, *The transription factor Nurr1 in human NT2 cells and hNT neurons.* Brain Res Dev Brain Res, 2003. 145(1): p. 107-15]. In addition, NT2N neurons also express Nurr1, an orphan nuclear receptor essential for the development, differentiation and survival of midbrain DA neurons.

Figure 7:
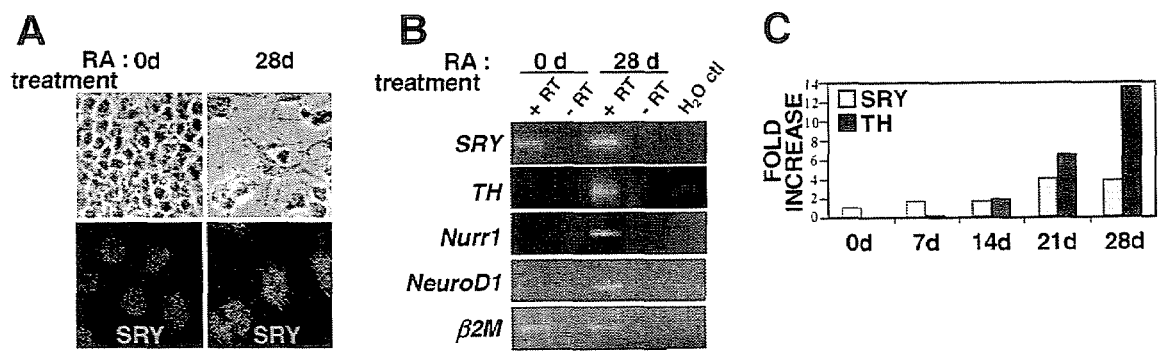
FIG. 7 shows (A) NT2 cells were differentiated with 10 μM all-trans RA for 28 days. Light microscopy shows the change in morphology of NT2 precursor cells into NT2N neurons. Following differentiation, SRY expression is predominantly nuclear with stronger fluorescence as visualized by immunofluorescence confocal microscopy using a SRY antibody generated and characterized in our laboratory (Sim et al., 2005). (B) RNA was isolated and used as template for RT-PCR. β-2-microgobulin was used as an RNA loading control. (C) By quantitative RT-PCR, SRY mRNA expression peaked at 21 day whilst TH mRNA was maximal at 28 days, suggesting that TH expression follows that of SRY.

The inventors show that SRY is expressed in NT2 precursor cells, using immunohistochemistry and RT-PCR (FIGS. 7A, B). Since these cells are reported to express TH upon differentiation, the inventors investigated the expression of SRY as NT2 precursor cells differentiate into NT2 neurons. This involved use of all-trans RA to differentiate NT2 cells into NT2N neurons (FIG. 7A). After 28 days of RA treatment, NT2Ns expressed TH, as well as Nurr1 and neural marker NeuroD1 (FIGS. 7B,C). From a time course experiment (FIGS. 7B,C), the inventors show by quantitative real time-PCR that TH expression, initially absent, was maximal at 28 days post RA treatment, and while SRY expression peaked at 21 days, suggesting that the upregulation of SRY precedes that of TH (FIG. 7B). Hence, the inventors established a cell culture model to study the effects of SRY in DA neurons. As NT2N cells adopt a DA phenotype, SRY and TH expression levels become elevated.

SRY Activation of TH Transcription

Figure 8:
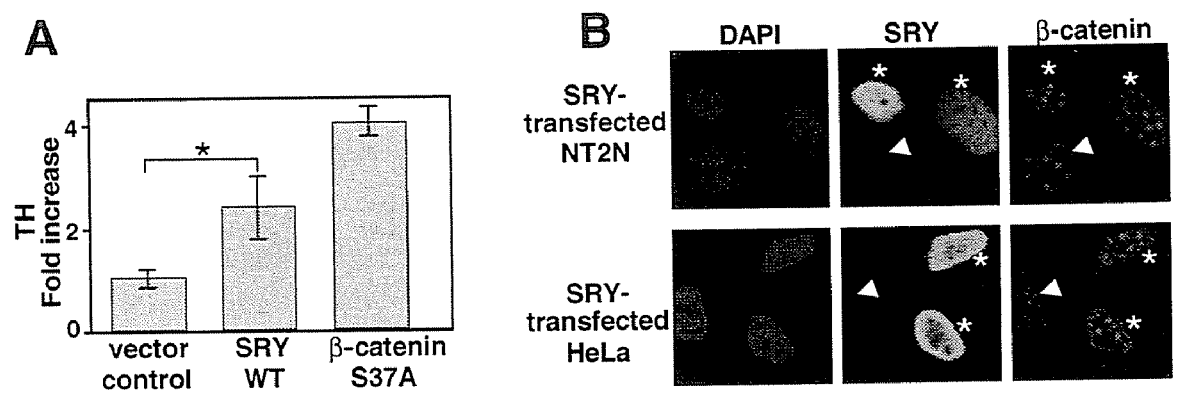
FIG. 8 shows (A) that overexpression of SRY activates TH expression in NT2N cells. (B) SRY increased accumulation of stabilized β-catenin in the nucleus of SRY-transfected NT2N neurons and in HeLa cells. Note that cells that stain for SRY (*) show higher levels of β-catenin in their nuclei compared to cells that do not (▶)).

To test if SRY can regulate TH transcription, the inventors co-overexpressed SRY and GFP in NT2N neurons by transient transfection. SRY/GFP positive cells were FAC sorted, RNA was extracted and TH mRNA levels were measured by qRT-PCR. SRY-transfected cells showed a 2.5 fold increase in TH expression when compared to cells tranfected with empty vector (FIG. 8A).

β-Catenin as a Potential Effector of SRY Activation of TH

As described above, treatment of ventral mesencephalic neuronal cultures with GSK3 β inhibitors which stabilize β-catenin increase the conversion of precursor cells into TH-positive DA neurons [Saunders-Pullman, R., Estrogens and Parkinson disease: neuroprotective, symptomatic, neither, or both? Endocrine, 2003. 21(1): p. 81-7]. Consistent with this, the inventors transfected a stabilized, underphosphorylated form of β-catenin (S37A) into the NT2N cells and observed a 4-fold increase in TH expression by qRT-PCR (FIG. 8A). Using an antibody that only recognizes the stabilized nuclear form of β-catenin (Upstate Biotech), the inventors found that these SRY-overexpressing NT2Ns and HeLa cells also show increased levels of stabilized β-catenin in their nuclei by immunofluorescence confocal microscopy (FIG. 8B). The increase accumulation of stabilized β-catenin in the nucleus was also similarly observed in exogenous SRY-overexpressing HeLa cells (FIG. 8B). Therefore these experiments point to a role for β-catenin as a mediator of SRY-induced TH expression. Thus we propose a mechanism whereby SRY stimulates TH expression by stabilization of β-catenin.

Identification of a Gonadal SRY Target Gene

Figure 9:
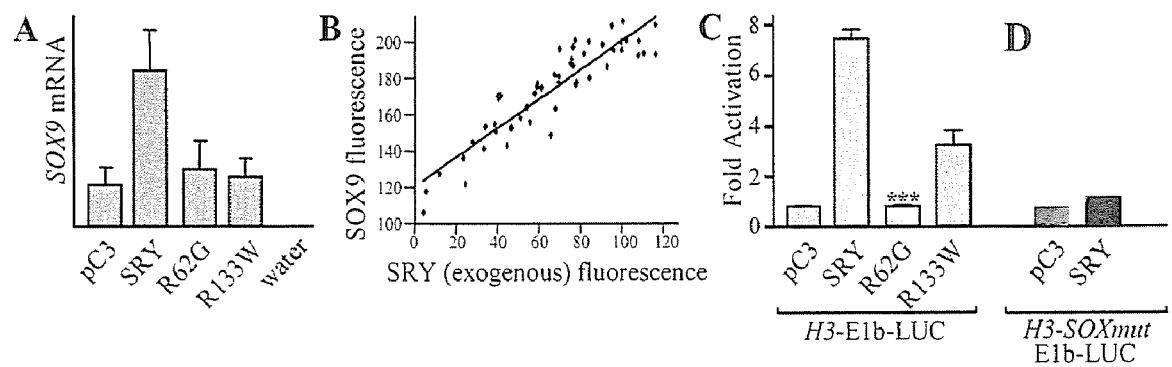
FIG. 9 shows that SRY regulates SOX9 mRNA, its likely target in the gonad (A) and protein expression (B) in transfected NT2 cells. This effect was lost when mutant SRY from XY females were used. (C) SRY activates the SOX9 enhancer, but SRY mutants fail to do so. Mutation of the SRY binding site in the SOX9 enhancer abolishes activation by SRY. (D) shows that SOX9 is expressed in glia, while SRY is in TH+ neurones so SOX9 is not a likely target of SRY in the SN.

A number of assays of SRY function that can be applied to SRY's role in the brain. No SRY target genes have been reported. In a search for SRY gonadal target genes, the inventors generated SRY-overexpressing precursor NT2 cells by transient transfection with an SRY plasmid. Quantitative (q) RT-PCR reveals a 3.5 fold increase in mRNA of the testis-determining gene, SOX9, mRNA and a positive correlation between SRY and SOX9 protein expression by immunofluorescence (FIG. 9A-B). Having identified SOX9 as a SRY target, the inventors showed that SRY directly activates a gonadal ridge-specific SOX9 enhancer region (data not presented). In vitro, SRY activates the SOX9 enhancer, whereas clinical SRY mutants from XY females fail to do so (FIG. 9C). Mutational analysis revealed that SRY binds to a single site within the SOX9 enhancer which, when mutated, abolishes activation (FIG. 9C). This is the first evidence that SRY activates a target gene, SOX9 by direct binding to its gonad-specific enhancer. By analogy, the inventors anticipate that SRY might act in a similar manner, in the SN, as a DNA binding transcriptional activator, to activate TH transcription, directly or indirectly.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An isolated neuronal cell transformed with a nucleic acid molecule encoding sex determining protein (SRY), wherein the transformed cell expresses SRY.

2. An isolated neuronal cell according to claim 1 wherein the nucleic acid encoding SRY is under the control of a heterologous promoter.

3. An isolated neuronal cell according to claim 1 wherein the cell is a stable, post-mitotic human NT2N cell.

4. A population of neuronal cells transformed with a nucleic acid molecule encoding sex determining protein (SRY), wherein the transformed cells express SRY.

5. A population of neuronal cells according to claim 4 wherein the nucleic acid molecule encoding SRY is under the control of a heterologous promoter.

6. A population of neuronal cells according to claim 4, wherein the population comprises at least 95% stable, post-mitotic human NT2N cells.

7. A population of neuronal cells according to claim 6, wherein the population comprises at least 96% stable, post-mitotic human NT2N cells.

8. A population of neuronal cells according to claim 7, wherein the population comprises at least 97% stable, post-mitotic human NT2N cells.

9. A population of neuronal cells according to claim 8, wherein the population comprises at least 98% stable, post-mitotic human NT2N cells.

10. A population of neuronal cells according to claim 9, wherein the population comprises at least 99% stable, post-mitotic human NT2N cells.

11. A population of neuronal cells according to claim 10, wherein the population comprises substantially pure, stable, post-mitotic human NT2N cells.

12. An isolated neuronal cell transformed with a nucleic acid molecule encoding sex determining protein (SRY), wherein the transformed cell expresses SRY and the nucleic acid encoding SRY is under the control of a heterologous promoter; and wherein the cell is a stable, post-mitotic human NT2N cell.

13. A population of neuronal cells transformed with a nucleic acid molecule encoding sex determining protein (SRY), wherein the transformed cells express SRY and the nucleic acid molecule encoding SRY is under the control of a heterologous promoter; and wherein the population comprises at least 95% stable, post-mitotic human NT2N cells.

14. A population of neuronal cells according to claim 13, wherein the population comprises at least 96% stable, post-mitotic human NT2N cells.

15. A population of neuronal cells according to claim 13, wherein the population comprises at least 97% stable, post-mitotic human NT2N cells.

16. A population of neuronal cells according to claim 13, wherein the population comprises at least 98% stable, post-mitotic human NT2N cells.

17. A population of neuronal cells according to claim 13, wherein the population comprises at least 99% stable, post-mitotic human NT2N cells.

18. A population of neuronal cells according to claim 13, wherein the population comprises substantially pure, stable, post-mitotic human NT2N cells.

* * * * *

SEQUENCE LISTING

<160> NUMBER OF SEQ ID NOS: 2

<210> SEQ ID NO 1
<211> LENGTH: 615
<212> TYPE: DNA
<213> ORGANISM: Human

<400> SEQUENCE: 1

```
atgcaatcat atgcttctgc tatgttaagc gtattcaaca gcgatgatta cagtccagct      60
gtgcaagaga atattcccgc tctccggaga agctcttcct tcctttgcac tgaaagctgt     120
aactctaagt atcagtgtga acgggagaa aacagtaaag caacgtcca ggatagagtg      180 aagcgaccca tgaacgcatt catcgtgtgg tctcgcgatc agaggcgcaa gatggctcta     240
gagaatccca gaatgcgaaa ctcagagatc agcaagcagc tgggatacca gtggaaaatg     300
cttactgaag ccgaaaaatg gccattcttc caggaggcac agaaattaca ggccatgcac     360
agagagaaat acccgaatta taagtatcga cctcgtcgga aggcgaagat gctgccgaag     420
aattgcagtt tgcttcccgc agatcccgct tcggtactct gcagcgaagt gcaactggac     480
aacaggttgt acagggatga ctgtacgaaa gccacacact caagaatgga gcaccagcta     540
ggccacttac cgcccatcaa cgcagccagc tcaccgcagc aacgggaccg ctacagccac     600
tggacaaagc tgtag                                                      615
```

<210> SEQ ID NO 2
<211> LENGTH: 204
<212> TYPE: PRT
<213> ORGANISM: Human

<400> SEQUENCE: 2

```
Met Gln Ser Tyr Ala Ser Ala Met Leu Ser Val Phe Asn Ser Asp Asp
 1               5                  10                  15

Tyr Ser Pro Ala Val Gln Glu Asn Ile Pro Ala Leu Arg Arg Ser Ser
                20                  25                  30

Ser Phe Leu Cys Thr Glu Ser Cys Asn Ser Lys Tyr Gln Cys Glu Thr
            35                  40                  45

Gly Glu Asn Ser Lys Gly Asn Val Gln Asp Arg Val Lys Arg Pro Met
        50                  55                  60

Asn Ala Phe Ile Val Trp Ser Arg Asp Gln Arg Arg Lys Met Ala Leu
65                  70                  75                  80

Glu Asn Pro Arg Met Arg Asn Ser Glu Ile Ser Lys Gln Leu Gly Tyr
                85                  90                  95

Gln Trp Lys Met Leu Thr Glu Ala Glu Lys Trp Pro Phe Phe Gln Glu
               100                 105                 110

Ala Gln Lys Leu Gln Ala Met His Arg Glu Lys Tyr Pro Asn Tyr Lys
           115                 120                 125

Tyr Arg Pro Arg Arg Lys Ala Lys Met Leu Pro Lys Asn Cys Ser Leu
       130                 135                 140

Leu Pro Ala Asp Pro Ala Ser Val Leu Cys Ser Glu Val Gln Leu Asp
145                 150                 155                 160

Asn Arg Leu Tyr Arg Asp Asp Cys Thr Lys Ala Thr His Ser Arg Met
               165                 170                 175
```

-continued

```
Glu His Gln Leu Gly His Leu Pro Pro Ile Asn Ala Ala Ser Ser Pro
            180                 185                 190

Gln Gln Arg Asp Arg Tyr Ser His Trp Thr Lys Leu
        195                 200
```